July 8, 1975 A. BARBERET ET AL Plant Pat. 3,739
CARNATION PLANT
Filed Feb. 19, 1974
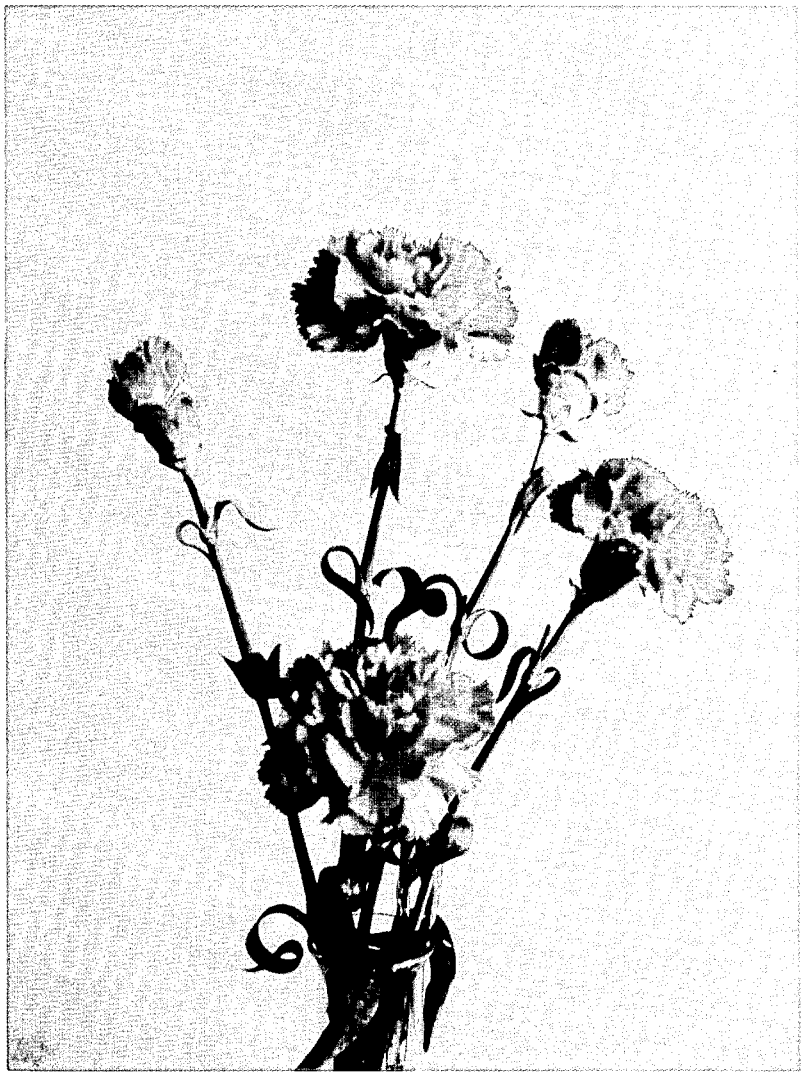

United States Patent

Plant Pat. 3,739

Patented July 8, 1975

3,739

CARNATION PLANT

Alexandre Barberet and Henri Blanc, La Londe, France, assignors to Laboratoire de Physiologie Vegetale de La Londe Barberet & Blanc, La Londe, France

Filed Feb. 19, 1974, Ser. No. 443,605

Int. Cl. A01h *5/00*

U.S. Cl. Plt.—73 1 Claim

ABSTRACT OF THE DISCLOSURE

A new variety of red carnation plant of the closed calyx or non-splitting, continuously blooming, American type characterized by a vigorous growth and precocious blooming habit and a very high wintertime production of medium sized flowers which retain the lively brightness of their red coloring during the low light of the winter season.

*Background of the New Plant*

This new carnation plant was developed by us during the course of breeding efforts carried on at La Londe, Les Maures, France, since 1967 with the object of producing a greenhouse carnation plant having a higher and more precocious production than the usual Sim varieties and a more stable wintertime color of its blossoms. The new plant originated as a seedling resulting from our crossing of selected varieties from breeding stock maintianed by us at our Laboratoire de Physiologie Vegetale, at La Londe, France, and was discovered in 1969 to possess the precocity and wintertime production characteristics that we were seeking.

Asexual propagation of this new plant by cuttings has been carried on under our direction, at La Londe, France, and many generations of such propagation have shown the novel characteristics of this plant to hold true and to be firmly fixed.

*Description of the Drawing*

Our new variety of carnation plant is illustrated by the accompanying photographic drawing which shows, in full color, a typical arrangement of buds, partially opened flowers, and full blooms; the colors shown being as nearly true as it is reasonably possible to obtain by conventional photographic procedures.

*Description of the New Plant*

The following is a detailed description of our new carnation plant variety based upon observations of greenhouse grown plants made at La Londe, France, in January 1973, the plants having been grown on raised benches containing an organic substratum of calcareous soil about 20 cm. deep. The color designations are according to the R.H.S. Colour Chart of The Royal Horticultural Society at London, England.

THE PLANT

Origin: Seedling.

Parentage:

- Seed Parent—Stock Variety #161B (unpatented).
- Pollen Parent—Stock Variety #245R (unpatented). These are unnamed varieties individually identified in our permanent records and maintained for breeding purposes in our personal collection of carnation plants at La Londe, France.

Classification:

- Botanic—Hybrid Dianthus Caryophyllus.
- Commercial—Greenhouse carnation for cut flowers.

Form: Leafy bush of the Sim type.

Height: 45 cm. at 6 months. Full grown plants flower at an average height of 90 cm. above the soil.

Growth: Upright and vigorous and very precocious.

Branches: Upright, with each principal stem developing an average of 4 branches which extend as floral stems each having 2 or 3 shoots growing from the lower one-third of its length.

Foliage: Abundant in quantity.

- Size of Leaf: Average length—15 cm. Average width—1.21 cm.
- Form of Leaf: Lanceolate, acuminate tip, and scabious. The leaves extend upwardly from the stem and then curve outwardly and downwardly.
- Texture: Smooth.
- Color: Leaves: Upper side—Greyed Green Group RHS 189A; under side—Green. Stems—Greyed Green RHS 189A. Nodes—Green RHS 138B and Greyed Green RHS 189A.

(The colors stated are to include nuances and are as close as can reasonably be averaged from the specimens observed.)

THE BUD

Size: Medium—rather short.

Form: Ovoid.

Diameter: 2.15 cm. average.

Opens: Slowly.

Calyx:

- Form: Generally pear shaped; conical at beginning, then cylindrical and finally ovoid to more-or-less spherical when the sepals open.
- Size: Large, 2.17 cm. in average length.
- Aspect: Smooth.
- Splitting: Calyx does not split.
- Color: Light Green.

Bracts: 4, opposed 2 by 2, united at the base and flattened against the calyx; the two outer bracts are reduced and overlap the two others.

Sepals:

- Shape: 1 cm. average length, generally curled back with a dried tip end.
- Number: Five.
- Striae: Parallel, plainly visible and yellowish color.

THE FLOWER

Blooming Habit: Early, profuse and continuous.

Size of Bloom: Medium.

Average diameter—6.93 cm. Average depth—4 cm.

Borne: Singly, after disbudding, for sale as a cut flower.

Opening: Regular, with progressive spreading of the guard petals and of the center petals; high centered at first, and finally forming a flower with a globular aspect.

Petalage: 71 to 99 petals, averaging about 82.

- Arrangement: More-or-less imbricated.
- Form: Fan shaped.
- Size: 5.5 x 3.5 cm.
- Color: A lively luminescent red, occasionally with small white stripes.

| | Young flower | Mature flower |
|---|---|---|
| Upper side | 45B, C and D | 45D–46C |
| Reverse side | 45B–46D | 45D–47C |

- Texture: Soft.
- Appearance: Satiny.

Petaloids: About 20 in number.

- Size: About one-half the size of the petals.
- Color: Red.

Peduncle: Erect, shorter than usual carnation, very strong and of average thickness. At full flower the stems are not brittle and are a little inclined from vertical.

Persistence: Petals hang on and dry.

Fragrance: Faintly perceptible.

Disease Resistance: Very good to the current diseases of carnations.

Lasting Quality:

On plant—12 days.

As cut flowers—7 days at about 23° C.

REPRODUCTIVE ORGANS

Stamens:

Anthers: 15 to 20, more-or-less undeveloped.

Filaments: Length 2.5 cm. Color: Whitish.

Pollen: Color—Yellowish.

Pistils: More often, 3 in number. Length.—3.5 cm. when ripened.

Stigmas: Color—Reddish.

Styles: Of rose tint in color.

Ovaries: Ribbed and more-or-less conical in shape, whitish color at the bottom, and more-or-less ochre yellow at the top.

Fruit: Fertile in summer. Shape: Ovoid. Color: At maturity—Green and ochreous.

Although the range of red caranations of the American type comprises numerous varieties which originated as sports of the cultivar William Sim (P.P. 699), the present invention is especially distinguished, not only by the manner of its origin, but also by its physical and physiological characteristics.

With respect to the William Sim originated varieties, the new plant is much more precocious and its wintertime production is significantly superior. The stems of the new plant are a little shorter and more rigid, its flower has a calyx that is very short, and above all, the flower coloring is stable and remains bright and lively throughout the winter season.

With respect to the variety Ember, or Longano (P.P. 3,537), the flower is smaller and its petal margin is more ruffled or dentate.

We claim:

1. A new and distinct variety of carnation plant substantially as herein shown and described, characterized by its precocity and abundant year around production of bright, medium sized blossoms, and the stability of the flower color which holds throughout the winter season.

No references cited.

ROBERT E. BAGWILL, Primary Examiner